(12) United States Patent
Kasai

(10) Patent No.: US 8,956,633 B2
(45) Date of Patent: Feb. 17, 2015

(54) POWDERY COSMETIC COMPOSITION

(75) Inventor: Takehiko Kasai, Kawasaki (JP)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/113,598

(22) PCT Filed: May 13, 2011

(86) PCT No.: PCT/JP2011/061604
§ 371 (c)(1),
(2), (4) Date: Oct. 24, 2013

(87) PCT Pub. No.: WO2012/157123
PCT Pub. Date: Nov. 22, 2012

(65) Prior Publication Data
US 2014/0050770 A1  Feb. 20, 2014

(51) Int. Cl.
| | | |
|---|---|---|
| A61K 8/00 | (2006.01) | |
| A61K 8/58 | (2006.01) | |
| A61K 8/19 | (2006.01) | |
| A61K 8/29 | (2006.01) | |
| A61Q 1/12 | (2006.01) | |
| A61K 8/27 | (2006.01) | |
| A61Q 1/02 | (2006.01) | |
| A61K 8/02 | (2006.01) | |

(52) U.S. Cl.
CPC . *A61K 8/585* (2013.01); *A61K 8/19* (2013.01); *A61K 8/29* (2013.01); *A61Q 1/12* (2013.01); *A61K 8/27* (2013.01); *A61Q 1/02* (2013.01); *A61K 8/022* (2013.01)
USPC .......................................................... 424/401

(58) Field of Classification Search
None
See application file for complete search history.

(56) References Cited

U.S. PATENT DOCUMENTS

| | | | |
|---|---|---|---|
| 3,615,972 | A | 10/1971 | Morehouse, Jr. et al. |
| 4,141,743 | A | 2/1979 | Grubba |
| 4,637,933 | A | 1/1987 | Zabotto nee Arribau et al. |
| 4,831,061 | A | 5/1989 | Hilaire et al. |
| 4,927,860 | A | 5/1990 | Hilaire et al. |
| 5,176,905 | A | 1/1993 | Ohno et al. |
| 5,234,682 | A | * 8/1993 | Macchio et al. ............... 424/69 |
| 5,538,793 | A | 7/1996 | Inokuchi et al. |
| 5,985,020 | A | 11/1999 | Andes et al. |
| 2005/0158257 | A1 | 7/2005 | Ogawa et al. |
| 2009/0311209 | A1 * | 12/2009 | Bujard ........................... 424/63 |

FOREIGN PATENT DOCUMENTS

| | | |
|---|---|---|
| EP | 0 056 219 A1 | 7/1982 |
| EP | 0 112 807 A2 | 7/1984 |
| EP | 0 242 219 A2 | 10/1987 |
| EP | 0 295 886 A2 | 12/1988 |
| EP | 0 303 530 A1 | 2/1989 |
| EP | 0 320 473 A1 | 6/1989 |
| EP | 0 348 372 A2 | 12/1989 |
| EP | 0 486 080 A2 | 5/1992 |
| EP | 0 765 656 A1 | 4/1997 |
| FR | 2 619 385 A1 | 2/1989 |
| FR | 2 929 111 A1 | 10/2009 |
| JP | 55-098261 | 7/1980 |
| JP | 61-194009 | 8/1986 |
| JP | 05-070325 | 3/1993 |
| JP | 09-227792 | 9/1997 |
| JP | 2000-191426 | 7/2000 |
| JP | 2000191426 * | 7/2000 |
| JP | 2000-517335 A | 12/2000 |
| JP | 2001-510784 A | 8/2001 |
| WO | 98/09611 A1 | 3/1998 |
| WO | 99/04757 A1 | 2/1999 |

OTHER PUBLICATIONS

International Search Report and Written Opinion for PCT/JP2011/061604.

* cited by examiner

*Primary Examiner* — Anand Desai
*Assistant Examiner* — Melissa Mercier
(74) *Attorney, Agent, or Firm* — The Marbury Law Group, PLLC

(57) ABSTRACT

The present invention relates to a cosmetic composition comprising a pulverulent phase comprising at least one composite powder including titanium dioxide and magnesium oxide. The cosmetic composition according to the present invention is at least comparable in terms of cosmetic effects with conventional cosmetic compositions comprising a conventional composite powder including titanium dioxide and zinc oxide. Therefore, the cosmetic composition is free of any potential problems which may be caused by zinc oxide which is commonly used in conventional cosmetic compositions.

19 Claims, No Drawings

POWDERY COSMETIC COMPOSITION

CROSS-REFERENCE TO RELATED APPLICATION

This is a national stage application of PCT/JP2011/061604, filed internationally on May 13, 2011, which is incorporated herein by reference in its entirety.

TECHNICAL FIELD

The present invention relates to a cosmetic composition comprising a novel composite powder instead of a conventional zinc oxide composite powder.

BACKGROUND ART

Sebum is a natural product from the sebaceous gland which, together with sweat produced by the eccrine or aprocrine glands, constitutes a natural moisturizer for the epidermis of the skin. It is reported that the sebaceous gland produces squalene, triglycerides, aliphatic waxes, cholesterol waxes and possibly free cholesterol (Stewart, M. E., Semin. Dermatol. 11, 100-105 (1992)). The action of bacterial lipases on the skin converts a variable portion of the triglycerides into free fatty acids. It is believed that the short color lasting or poor color staying may be attributed to fatty acids.

Thus, it would be advantageous to remove fatty acids from the surface of the skin because this removal would reduce the unfavorable effects by sebum such as short lasting and poor staying power of make-up on that surface.

There are some known substances which can absorb oily ingredients such as fatty acids. For example, JP-A-H09-227792 cites zinc oxide particles as a sebum absorber. However, zinc oxide particles, in particular zinc oxide nano-particles are suspected to have environmental toxicity.

DISCLOSURE OF INVENTION

Thus, an objective of the present invention is to provide a cosmetic composition including a substituent for conventional zinc oxide particles, without sacrificing cosmetic properties.

The above objective of the present invention can be achieved by a cosmetic composition comprising a pulverulent phase comprising at least one composite powder including titanium dioxide and magnesium oxide.

It is preferable that the weight ratio of the titanium dioxide to the magnesium oxide in the composite powder be 1 or more.

It is preferable that the composite powder further comprise at least one silicone compound, preferably a methicone or a dimethicone/methicone copolymer.

It is preferable that the composite powder further comprise at least one filler, preferably talc.

The amount of the composite powder may be 1 to 50 wt %, preferably 3 to 30 wt %, and more preferably 5 to 20 wt %, relative to the total weight of the pulverulent phase.

It is preferable that the pulverulent phase further comprise at least one additional filler.

It is preferable that the additional filler has been surface-treated with a surface treatment agent comprising at least one amino acid and/or a derivative thereof. The amino acid may be selected from the group consisting of proline, hydroxyproline, alanine, glycine, sarcosine, aspartic acid, and glutamic acid.

It is preferable that the additional filler be selected from the group consisting of talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, and hydroxyapatite. It is more preferable that additional filler be mica.

It is preferable that the additional filler be coated with a mixture of at least one fatty acid, such as a $C_{12}$-$C_{18}$ fatty acid, and/or a salt of the fatty acid, and
(a) at least one selected from proline, hydroxyproline and derivatives thereof; and/or
(b) at least one selected from alanine, glycine, sarcosine and derivatives thereof; and/or
(c) at least one selected from aspartic acid, glutamic acid and derivatives thereof.

It is most preferable that the additional filler be a mica coated with a mixture of palmitic acid, palmitoylproline, sodium palmitoyl sarcosinate, and magnesium palmitoyl glutamate.

The amount of the pulverulent phase may be 10 to 99 wt %, preferably 30 to 95 wt %, and more preferably 50 to 90 wt %, relative to the total weight of the composition.

It is preferable that the cosmetic composition according to the present invention further comprise at least one dyestuff.

It is preferable that the cosmetic composition according to the present invention further comprise at least one oil.

The present invention also relates to a process for making-up skin with a cosmetic composition as explained above.

BEST MODE FOR CARRYING OUT OF THE INVENTION

After diligent research, the inventors have discovered that it is possible to use a composite powder including titanium dioxide and magnesium oxide, preferably with a methicone or a dimethicone/methicone copolymer, and more preferably with talc, can be used as a preferable substituent for a conventional zinc oxide powder.

Thus, the cosmetic composition according to the present invention comprises at least one composite powder including titanium dioxide and magnesium oxide, preferably with a methicone or a dimethicone/methicone copolymer, and more preferably with talc.

The cosmetic composition according to the present invention can have cosmetic effects which are comparable with those of a conventional cosmetic composition comprising a zinc oxide powder, without any environmental toxicity caused possibly by zinc oxide.

Furthermore, the use of the above composite powder can provide a cosmetic composition with better immediate matte effects and higher UV protection effects, as compared to the use of the zinc oxide powder.

The cosmetic composition according to the present invention will be explained below in a detailed manner.
(Pulverulent Phase)

The cosmetic composition according to the present invention comprises a pulverulent phase, as a main component. The total amount of the pulverulent phase, may be from 5 to 100% by weight, preferably 10 to 99% by weight, more preferably 30 to 95% by weight, and further more preferably 50 to 90% by weight relative to the total weight of the cosmetic composition. Thus, the cosmetic composition according to the present invention may be in the form of a powdery cosmetic composition.

The pulverulent phase may optionally comprise only a small amount of zinc oxide. It is preferable that the amount of zinc oxide is 1 wt % or less, 0.1 wt % or less, 0.01 wt % or less, or 0.001 wt % or less, relative to the total weight of the pulverulent phase. It is most preferable that the cosmetic composition according to the present invention comprise no zinc oxide.

(Composite Powder)

The pulverulent phase comprises at least one composite powder including titanium dioxide and magnesium oxide. It is preferable that the weight ratio of the titanium dioxide to the magnesium oxide in the composite powder be 1 or more, preferably from 1 to 1.5.

The composite powder may further comprise at least one silicone compound. The silicone compound may preferably be organohydrogenpolysiloxane. In particular, the organohydrogenpolysiloxane may preferably a methicone or a dimethicone/methicone copolymer.

The composite-powder may further comprise at least one filler. As used herein, the term "filler" means a substantially uncolored compound that is solid at room temperature and atmospheric pressure, and insoluble in the various ingredients of the composition, even when these ingredients are brought to a temperature above room temperature. The filler may or may not be porous.

The filler can be inorganic or organic, surface-treated or non-surface treated, and can be of spherical or oblong shape, whatever the crystallographic form (for example, sheet, cubic, hexagonal, orthorhombic, and the like). The filler may preferably be a non-spherical inorganic filler.

The material of the filler is not limited, but is preferably selected from the group consisting of talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, and hydroxyapatite. As the material, talc, mica, kaolin, sericite are more preferable, and talc and mica are even more preferable, and talc is most preferable.

The filler may preferably be pre-coated with at least one oxide or hydroxide of a metal element such as aluminum, calcium, magnesium, cerium, silicon, zirconium, titanium, zinc, iron, cobalt, manganese, nickel, and tin. Aluminum hydroxide is more preferable.

The composite powder used in the present invention can be prepared in accordance with conventional methods in the art.

For example, the composite powder may be prepared by coating a filler such as a talc with titanium dioxide and magnesium oxide, and further coating with at least one silicone compound such as a methicone or a dimethicone/methicone copolymer.

The coating of a filler with titanium dioxide and magnesium oxide may be performed by dispersing the filler in an aqueous liquid prepared by dissolving a water-soluble magnesium salt into an aqueous medium and by dispersing titanium dioxide, followed by adding an inorganic hydroxide such as sodium hydroxide and potassium hydroxide; filtering out the filler from the aqueous liquid; and drying the filler.

Then, the further coating of the coated filler as above may be performed by adding a liquid prepared by dissolving at least one silicone compound such as a methicone or a dimethicone/methicone copolymer in a volatile solvent to the coated filler, and stirring the mixture; and then drying the mixture. As the volatile solvent, for example, alcohols such as ethanol and isopropanol; hydrocarbons such as hexane, toluene and xylene; ketones such as methylethylketone; ethers such as dimethylethers; and volatile silicones such as cyclopentacyloxane, may be used.

Alternatively, titanium dioxide and magnesium oxide may be mixed with a filler such as a talc in a mixer, and then at least one silicone compound such as a methicone or a dimethicone/methicone copolymer may be added to the mixer, followed by pulverizing and drying.

The amount of the composite powder in the pulverulent phase is not limited, but may be 1 to 50 wt %, preferably 3 to 30 wt %, and more preferably 5 to 20 wt %, relative to the total weight of the pulverulent phase. Thus, the amount of the composite powder in the cosmetic composition may be 1 to 40 wt %, preferably 3 to 25 wt %, and more preferably 5 to 15 wt %, relative to the total weight of the pulverulent phase.

(Additional Filler)

The cosmetic composition according to the present invention may comprise at least one additional filler.

The additional filler may be spherical or non-spherical filler.

The spherical filler may be organic or inorganic.

As the inorganic spherical filler, mention may be made of silica microspheres, for example, of open porosity, such as hollow silica microspheres, including the products "Silica Beads SP 700/HA(R)" and "Silica Beads SB 700(R)" from the company Maprecos, and "Sunspheres H-33(R)" and "Sunspheres H-51(R)" from the company Asahi Glass.

It is preferable that the spherical filler is chosen from organic spherical fillers.

In some embodiments, the organic spherical fillers are not film-forming, i.e., they do not form a continuous film when deposited onto keratin layers such as the skin.

The organic spherical filler may be chosen, for example, from: (meth)acrylic or (meth)acrylate powders, for example, polymethylmethacrylate powders; polyacrylonitrile powders; polyurethane powders; polyamide powders; organopolysiloxane powders; and the like, as well as a mixture thereof.

According to one embodiment, the composition may comprise at least one spherical filler of polymethylmethacrylate.

The polymethylmethacrylate powder may be in the form of hollow or solid white spherical particles generally with a number-average size of micrometer order, for example, ranging from 3 to 15 microns and, further, for example, ranging from 3 to 10 microns. As used herein, the expression "number-average size" means the size given by the statistical particle size distribution to half of the population, referred to as D50.

It is also possible to characterize the polymethylmethacrylate particles by their density, which can vary, for example, as a function of the size of the spherical cavity of the particles.

In accordance with the embodiments disclosed herein, this density is assessed according to the following protocol, referred to as the packed density: m=40 g of powder is poured into a measuring cylinder; the measuring cylinder is then placed on a Stav 2003 machine from Stampf Volumeter; the measuring cylinder is then subjected to 1500 packing motions; the final volume Vf of packed powder is then measured directly on the measuring cylinder. The packed density is determined by the ratio m/Vf, in this instance 40/Vf (Vf being expressed in $cm^3$ and m in g).

For example, the density of the polymethylmethacrylate powder that may be used in the embodiments disclosed herein may range, for example, from 0.3 to 1.5, further, for example, from 0.5 to 1.5 and, even further, for example, from 1 to 1.5.

As non-limiting illustrations of the polymethylmethacrylate powder that is suitable for use in the composition disclosed herein, mention may be made, for example, of the polymethylmethacrylate particles sold by the company Matsumoto Yushi Co. under the name "Micropearl M100", by the company LCW under the name "Covabead LH 85" and those sold by the company Nihon Junyaku under the name "Jurymer MB1".

The polymethylmethacrylate powder may be present in an amount ranging from 1% to 20% by weight, for example, ranging from 2% to 15% by weight and further, for example, ranging from 3% to 10% by weight, relative to the total weight of the composition.

According to one embodiment, the composition may comprise at least one spherical filler of polyacrylonitrile.

The polyacrylonitrile powder may be chosen from acrylonitrile homopolymer powders and acrylonitrile copolymer powders, and, for example, expanded hollow particles of acrylonitrile homopolymer or copolymer. For example, the powders may be made of any expanded acrylonitrile homopolymer or copolymer that is non-toxic and a non-irritant to the skin.

For example, the mass per unit volume of the particles is chosen in the range from 15 kg/m$^3$ to 200 kg/m$^3$, for example, from 40 kg/m$^3$ to 120 kg/m$^3$ and even further, for example, from 60 kg/m$^3$ to 80 kg/m$^3$. To obtain this low mass per unit volume, expanded polymer or copolymer particles, for example, based on acrylonitrile and on an acrylic or styrene monomer and/or on vinylidene chloride, may be used.

It is possible to use, for example, a copolymer comprising: from 0% to 60% of units derived from vinylidene chloride, from 20% to 90% of units derived from acrylonitrile and from 0% to 50% of units derived from an acrylic or styrene monomer, wherein the sum of the percentages (by weight) is equal to 100. The acrylic monomer may, for example, be a methyl or ethyl acrylate or methacrylate. The styrene monomer may, for example, be α-methylstyrene or styrene.

In one embodiment, the powders used in the composition disclosed herein are chosen from hollow particles of an expanded copolymer of vinylidene chloride and of acrylonitrile or of vinylidene chloride and of acrylonitrile and of methacrylate. These powders may be dry or hydrated.

The powders may be obtained, for example, according to the processes disclosed in Patent and Patent Application Nos. EP 56219, EP 348372, EP 486080, EP 320473, EP 112807 and U.S. Pat. No. 3,615,972.

The internal cavity of the powder particles in principle comprises at least one gas, which may be chosen from air, nitrogen, and hydrocarbons, such as isobutane and isopentane.

In some embodiments, the powder particles disclosed herein have a particle size ranging from 1 μm to 80 μm, for example, ranging from 10 μm to 50 μm and from 10 μm to 30 μm.

The powder particles may be chosen, for example, from expanded terpolymer micro-spheres of vinylidene chloride, of acrylonitrile and of methacrylate, sold under the brand name Expancel by the company Expancel under the references 551 DE 50 (particle size of 40 μm), 551 DE 20 (particle size of 30 μm and mass per unit volume of 65 kg/m$^3$), 551 DE 12 (particle size of 12 μm), 551 DE 80 (particle size of 80 μm) and 461 DE 50 (particle size of 50 μm). It is also possible to use microspheres formed from the same expanded terpolymer having a particle size of 8 μm and a mass per unit volume of 70 kg/m$^3$, referred to hereinbelow as EL 23, or having a particle size of 34 μm and a mass per unit volume of 20 kg/m$^3$, referred to hereinbelow as EL 43.

The acrylonitrile powder may be present in the composition disclosed herein in an amount ranging from 0.02% to 2% by weight, for example, ranging from 0.1% to 1.5% by weight, and, further, for example, ranging from 0.1% to 1.2% by weight, relative to the total weight of the composition.

According to one embodiment, the composition may comprise at least one spherical filler of polyurethane.

The polyurethane powder may be a powder of a copolymer of hexamethylene diisocyanate and trimethylol hexyl lactone. Such a polyurethane powder is sold, for example, under the names "Plastic Powder D-400" and "Plastic Powder D-800" by the company Toshiki. Other polyurethane powders that may be used include the product sold under the name "Plastic Powder CS-400" by the company Toshiki.

The polyurethane powder may be present in the composition disclosed herein in an amount ranging from 1% to 20% by weight, for example, ranging from 2% to 15% by weight and, further, for example, ranging from 3% to 10% by weight, relative to the total weight of the composition.

According to one embodiment, the composition may comprise at least one spherical filler of polyamide.

Polyamide powders useful in the invention may be those listed under the CTFA name of "Nylon 12" or "Nylon 6". A mixture of particles and, for example, a mixture of Nylon-6 and Nylon-12 may be used.

The polyamide powder particles used in the invention include those sold under the names "Orgasol" by the company Atochem. The process for obtaining these particles is, for example, the process described in document FR-A-2 619 385 or in document EP-A-303 530. These polyamide powder particles are moreover known according to their various physicochemical properties under the name "polyamide 12" or "polyamide 6".

Particles useful in the present invention may also include those sold under the name SP500 by the company TORAY.

The polyamide powder may be present in the composition disclosed herein in an amount ranging from 1% to 20% by weight, for example, ranging from 2% to 15% by weight and, further, for example, ranging from 3% to 10% by weight, relative to the total weight of the composition.

According to a preferred embodiment, the composition may comprise at least one spherical filler of organopolysiloxane.

The organopolysiloxane may be elastomeric or non-elastomeric. It is preferable to use elastomeric organopolysiloxane powder or organopolysiloxane elastomer powder.

The elastomeric organopolysiloxane may, for example, be crosslinked and may be obtained
via a crosslinking addition reaction of diorganopolysiloxane comprising at least one hydrogen linked to silicon and of diorganopolysiloxane comprising at least one ethylenically unsaturated group linked to silicon, preferably, in the presence, for example, of a platinum catalyst; or
via a dehydrogenation crosslinking condensation reaction between a diorganopolysiloxane comprising at least one hydroxyl end group and a diorganopolysiloxane comprising at least one hydrogen linked to silicon, preferably, in the presence of, for example, an organotin compound; or
via a crosslinking condensation reaction of a diorganopolysiloxane comprising at least one hydroxyl end group and of a hydrolysable organopolysilane; or
via thermal crosslinking of organopolysiloxane, preferably, in the presence of, for example, an organoperoxide catalyst; or
via crosslinking of organopolysiloxane by high-energy radiation such as gamma rays, ultraviolet rays or an electron beam.

In one embodiment, the elastomeric organopolysiloxane powder is crosslinked and is obtained via a crosslinking addition reaction of a diorganopolysiloxane (B2) comprising at least two hydrogens, each linked to a silicon, and of a diorganopolysiloxane (A2) comprising at least two ethylenically unsaturated groups linked to silicon, preferably, in the presence of, for example, a platinum catalyst (C2), for instance as described in Patent Application No. EP-A-295886.

For example, the organopolysiloxane may be obtained via a reaction of dimethylpolysiloxane comprising dimethylvinylsiloxy end groups and of methylhydrogenopolysiloxane comprising trimethylsiloxy end groups, in the presence of a platinum catalyst.

Compound (A2) is the base reagent for the formation of elastomeric organopolysiloxane and the crosslinking takes place via an addition reaction of compound (A2) with compound (B2) in the presence of the catalyst (C2).

Compound (A2) may, for example, be a diorganopolysiloxane comprising at least two lower alkenyl groups (for example C2-C4); the lower alkenyl group may be chosen from vinyl, allyl and propenyl groups. These lower alkenyl groups may be located in any position of the organopolysiloxane molecule, but in one embodiment are located at the ends of the organopolysiloxane molecule. The organopolysiloxane (A2) may have a branched-chain, linear-chain, cyclic or network structure; in one embodiment, the linear-chain structure may be used. Compound (A2) may have a viscosity ranging from the liquid state to the gum state. For example, compound (A2) may have a viscosity of at least 100 centistokes at 25° C.

The organopolysiloxanes (A2) may be chosen from methylvinylsiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxane-methylvinylsiloxane copolymers comprising dimethylvinylsiloxy end groups, dimethyl-siloxane-methylvinylsiloxane copolymers comprising trimethylsiloxy end groups, dimethylsiloxane-methylphenylsiloxane-methylvinylsiloxane copolymers comprising trimethylsiloxy end groups, methyl(3,3,3-trifluoropropyl)polysiloxane comprising dimethylvinylsiloxy end groups, and dimethylsiloxane-methyl(3,3,3-trifluoropropyl)siloxane copolymers comprising dimethylvinylsiloxy end groups.

Compound (B2) may, for example, be an organopolysiloxane comprising at least two hydrogens linked to silicon in each molecule and is thus the crosslinking agent for the compound (A2).

In one embodiment, the sum of the number of ethylenic groups per molecule of compound (A2) and the number of hydrogen atoms linked to silicon per molecule of compound (B2) is at least 4.

Compound (B2) may be of any molecular structure. In one embodiment, compound (B2) is of linear-chain or branched-chain structure or cyclic structure.

Compound (B2) may have a viscosity at 25° C. ranging from 1 to 50000 centistokes, for example, in order to have good miscibility with compound (A2).

In one embodiment, compound (B2) may be added in an amount such that the molecular ratio between the total amount of hydrogen atoms linked to silicon in compound (B2) and the total amount of all the ethylenically unsaturated groups in compound (A2) is within the range from 1:1 to 20:1.

Compound (B2) may be chosen from methylhydrogenopolysiloxanes comprising trimethylsiloxy end groups, dimethylsiloxane-methylhydrogenosiloxane copolymers comprising trimethylsiloxy end groups, and cyclic dimethylsiloxane-methylhydrogenosiloxane copolymers.

Compound (C2) is the crosslinking reaction catalyst, and may, for example, be chosen from chloroplatinic acid, chloroplatinic acid-olefin complexes, chloroplatinic acid-alkenylsiloxane complexes, chloroplatinic acid-diketone complexes, platinum black, and platinum on a support.

The catalyst (C2) may, for example, be added in an amount ranging from 0.1 to 1000 parts by weight and, further, for example, from 1 to 100 parts by weight, as clean platinum metal, per 1000 parts by weight of the total amount of compounds (A2) and (B2).

Other organic groups may be linked to silicon in the organopolysiloxanes (A2) and (B2) described previously, for example, alkyl groups, such as methyl, ethyl, propyl, butyl or octyl; substituted alkyl groups, such as 2-phenylethyl, 2-phenylpropyl or 3,3,3-tri-fluoropropyl; aryl groups, such as phenyl, tolyl or xylyl; substituted aryl groups, such as phenylethyl; and substituted monovalent hydrocarbon-based groups, such as an epoxy group, a carboxylate ester group or a mercapto group.

In some embodiments, the at least one elastomeric organopolysiloxane powder may, for example, be chosen from non-emulsifying elastomers. As used herein, the term "non-emulsifying" means organopolysiloxane elastomers not comprising a hydrophilic chain, such as polyoxyalkylene or polyglycerolated units.

Spherical elastomeric organopolysiloxanes are, for example, described in Patent Application Nos. JP-A-61-194 009, EP-A-242 219, EP-A-295 886 and EP-A-765 656, the contents of which are incorporated by reference.

Elastomer organopolysiloxane powders that may be used include those sold under the names "Dow Corning 9505 Powder" and "Dow Corning 9506 Powder" by the company Dow Corning; these powders have the INCI name: dimethicone/vinyl dimethicone crosspolymer.

The elastomeric organopolysiloxane powder may, for example, be chosen from elastomeric organopolysiloxane powders coated with silicone resin, for example, with silsesquioxane resin, as described, for example, in U.S. Pat. No. 5,538,793, the content of which is incorporated by way of reference. Such elastomeric powders are sold under the names "KSP-100", "KSP-101", "KSP-102", "KSP-103", "KSP-104" and "KSP-105" by the company Shin-Etsu, and have the INCI name: vinyl dimethicone/methicone silsesquioxane crosspolymer.

Other elastomeric organopolysiloxanes in the form of spherical powders may be powders of hybrid silicone functionalized with fluoroalkyl groups, sold, for example, under the name "KSP-200" by the company Shin-Etsu and powders of hybrid silicones functionalized with phenyl groups, sold, for example, under the name "KSP-300" by the company Shin-Etsu.

In one embodiment, the composition may, for example, comprise at least two powders of elastomeric organopolysiloxane chosen from elastomeric organopolysiloxane powders coated with silicone resin, for example, with silsesquioxane resin, as described previously.

In some embodiments, the composition disclosed herein may comprise at least one elastomeric organopolysiloxane spherical powder chosen from elastomeric organopolysiloxane spherical powders coated with at least one silicone resin, for example, with silsesquioxane resin, in an amount ranging from 1% to 25% by weight, for example, from 1% to 15% by weight, further, for example, ranging from 2% to 8% by weight and, even further, for example, ranging from 3% to 7% by weight, relative to the total weight of the composition.

The composition disclosed herein may comprise a mixture of at least one elastomeric organopolyeiloxane spherical powder chosen from elastomeric organopolysiloxane spherical powders coated with silicone resin, for example, with silsesquioxane resin, and uncoated elastomeric organopolysiloxane spherical powders. In such a mixture, the elastomeric organopolysiloxane spherical powders coated with silicone resin, for example, with silsesquioxane resin, may be present in an amount ranging from 1% to 10% by weight, for example, ranging from 2% to 8% by weight and, further, for example, ranging from 3% to 7% by weight, relative to the total weight of the composition; the uncoated elastomeric organopolysiloxane spherical powders may be present in an amount ranging from 1% to 10% by weight, for example, ranging from 2% to 8% by weight and, further, for example, ranging from 3% to 7% by weight, relative to the total weight of the composition.

The elastomeric organopolysiloxane powder may be present in the composition disclosed herein in an amount ranging from 50% to 100% by weight, for example, ranging from 50% to 90% by weight and, further, for example, ranging from 50% to 80% by weight, relative to the total weight of the spherical fillers.

The composition disclosed herein may comprise the elastomeric organopolysiloxane powder in an amount ranging from 1% to 30% by weight, for example, ranging from 2% to 20% by weight, further, for example, ranging from 3% to 15% by weight and, even further, for example, ranging from 5% to 10% by weight, relative to the total weight of the composition.

The composition disclosed herein may comprise the spherical filler in an amount ranging from 1% to 50% by weight, for example, ranging from 5% to 40% by weight, further, for example, ranging from 10% to 30% by weight and, even further, for example, ranging from 15% to 25% by weight, relative to the total weight of the composition.

The "non-spherical" filler may be of any form other than spherical, for example, platelet-shaped, spherical, and oblong, irrespective of their crystallographic form (for example lamellar, cubic, hexagonal, and orthorhombic). In a preferred embodiment, the non-spherical filler is in a lamellar form. Preferably, the non-spherical filler has a high aspect ratio of 10 or more. The aspect ratio may be 20 or more or 50 or more. The aspect ratio can be determined by the average thickness and the average length according to the formula: aspect ratio=length/thickness.

The term "average particle size" here means the size given by the statistical particle size distribution to half of the population, referred to as D50. The average particle size can, for example, be measured with Mastersizer 2000 by Malvern Corp.

The non-spherical filler may have an average particle size of less than 20 μm, preferably less than 10 μm, for example, from 1 to 6 μm.

The material of the non-spherical filler is not limited, but is preferably selected from the group consisting of talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, and hydroxyapatite. As the material, talc, mica, kaolin, sericite are more preferable, and talc and mica are even more preferable. A mixture of these may be used as the material for the non-spherical fillers. The materials of the two fillers may be the same or different. In a preferred embodiment, it is talc or mica, and more preferably mica.

According to the present invention, the non-spherical filler may have been surface-treated with a surface treatment agent comprising at least one silicone oil.

The silicone oil may be selected from polydialkylsiloxanes such as polydimethylsiloxane, polyalkylaryldiloxanes such as polymethylphenylsiloxane, polydiarylsiloxanes such as polydiphenylsiloxanes, polyalkylhydrogensiloxanes such as methylhydrogenpolysiloxane, and modified-polysiloxanes.

The modified-polysiloxanes may be chosen from the following formulae:

($a^1$) modified polysiloxanes bearing polyethers, chosen from compounds of formula (III):

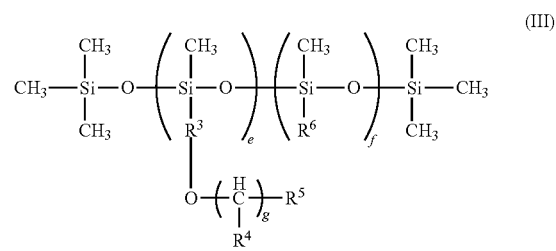

wherein
$R^3$ comprises —$(CH_2)_h$—;
$R^4$ comprises —$(CH_2)_i$—$CH_3$;
$R^5$ is chosen from —OH, —COOH, —CH=$CH_2$, —C($CH_3$)=$CH_2$ and —$(CH_2)_j$—$CH_3$;
$R^6$ comprises —$(CH_2)_k$—$CH_2$;
g and h independently range from 1 to 15;
j and k independently range from 0 to 15;
e ranges from 1 to 50; and
f ranges from 1 to 300;

($a^2$) modified polysiloxanes bearing polyesters, chosen from compounds of formula (IV):

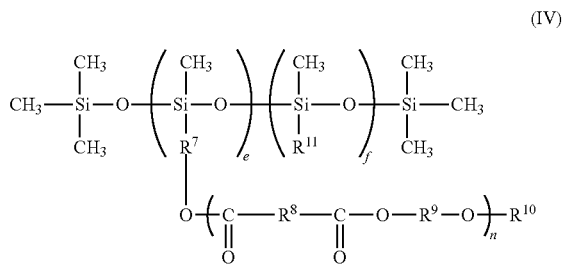

wherein
$R^7$, $R^8$ and $R^9$ are independently chosen from —$(CH_2)_q$—;
$R^{10}$ is chosen from —OH, —COOH, —CH=$CH_2$, —C($CH_3$)=$CH_2$ and —$(CH_2)_r$—$CH_3$;
$R^{11}$ comprises —$(CH_2)_s$—$CH_3$;
n and q independently range from 1 to 15;
r and s independently range from 0 to 15;
e ranges from 1 to 50; and
f ranges from 1 to 300;

(a³) modified polysiloxanes bearing epoxy radicals, chosen from compounds of formula (V):

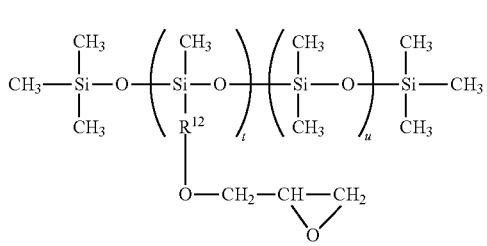

wherein
R$^{12}$ comprises —(CH$_2$)$_v$—;
v ranges from 1 to 15;
t ranges from 1 to 50; and
u ranges from 1 to 300;
and
mixtures thereof.

Alternatively, the modified-polysiloxane may be chosen from compounds of formula (VI):

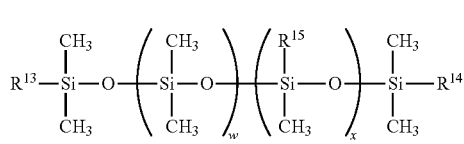

wherein
R$^{13}$ and R$^{14}$ are independently chosen from —OH, R$^{16}$OH and R$^{17}$COOH;
R$^{15}$ is chosen from —CH$_3$ and —C$_6$H$_5$;
R$^{16}$ and R$^{17}$ comprise —(CH$_2$)$_y$—;
y ranges from 1 to 15;
w ranges from 1 to 200; and
x ranges from 0 to 100.

It is preferable that the silicone oil is a polydialkylsiloxane such as polydimethylsiloxane or a mixture of polydialkylsiloxanes.

The surface treatment agent for the non-spherical filler may comprise at least one dimethylpolysiloxane.

According to one embodiment of the present invention, the surface treatment of the non-spherical filler may be chosen from the following treatments:
PEG-silicone treatments, for instance the AQ surface treatment sold by LCW;
methicone treatments, for instance the SI surface treatment sold by LCW; and
dimethicone treatments, for instance the Covasil 3.05 surface treatment sold by LCW, or the SA surface treatments sold by Miyoshi Kasei, and in particular the product SA-TA-13R sold by MIYOSHI KASEI (INCI Name Talc and dimethicone).

In a preferred embodiment, a dimethicone-treated talc can be used as the non-spherical filler.

According to the present invention, the non-spherical filler may have been surface-treated with a surface treatment agent comprising at least one amino acid and/or a derivative thereof.

The amino acid may preferably be selected from the group consisting of proline, hydroxyproline, alanine, glycine, sarcosine, aspartic acid, and glutamic acid.

The amino acids may be L-isomers or a mixture of L-isomers and D-isomers.

It is preferable that the non-spherical filler has been coated with:
(a) at least one selected from proline, hydroxyproline and derivatives thereof; and/or
(b) at least one selected from alanine, glycine, sarcosine and derivatives thereof; and/or
(c) at least one selected from aspartic acid, glutamic acid and derivatives thereof.

The derivatives of the amino acids may be selected from salts of the amino acids, and N-acylated amino acids and salts thereof.

It is preferable that two of the components (a) to (c) be used together, and it is more preferable that all of the components (a) to (c) be used together. If two or more of the components (a) to (c) are used, the type of the derivatives and/or salts may be the same or different.

The N-acyl group of the N-acylated amino acid may be a linear or branched, saturated or unsaturated acyl group with C$_8$-C$_{22}$ carbon atoms, preferably C$_{12}$-C$_{18}$ carbon atoms. It is preferable that the N-acyl group is a linear saturated acyl group, such as a palmitoyl group.

The salt of the amino acid or the N-acylated amino acid is not limited but may be in the form of a metal salt with a metal element such as Na, K, Ba, Zn, Ca, Mg, Fe, Zr, Co, Al, Ti and the like; an onium salt such as an ammonium salt; and a salt with an organic alkanolamine such as monoethanolamine, diethanolamine, triethanolamine, 2-amino-2-methylpropanol, 2-amino-2-methyl-1,3-propanediol, and triisopropanolamine. It is preferable that the salt is a metal salt with Na, K, Ca, Mg or Al.

It is more preferable that the non-spherical filler has been coated with a mixture (referred to as "lipo-amino acid composition") of at least one fatty acid, such as a C$_{12}$-C$_{18}$ fatty acid, and/or a salt of the fatty acid, and
(a) at least one selected from proline, hydroxyproline and derivatives thereof; and/or
(b) at least one selected from alanine, glycine, sarcosine and derivatives thereof; and/or
(c) at least one selected from aspartic acid, glutamic acid and derivatives thereof.

As the fatty acid, a linear, branched or cyclic fatty acid, preferably C$_{12}$-C$_{18}$, can be used. A plurality of fatty acids may be used. As examples of the fatty acid, mention may be made of lauric acid, myristic acid, isomyristic acid, palmitic acid, isopalmitic acid, stearic acid, isostearic acid, oleic acid, myristoleic acid, elaidic acid, linoleic acid, and linolenic acid. As example of the salt of the fatty acid, mention may be made of a metal salt with a metal element such as Na, K, Ba, Zn, Ca, Mg, Fe, Zr, Co, Al, Ti or the like. Lauric acid, myristic acid, palmitic acid and stearic acid as well as a metal salt thereof with Na, K, Ca, Al or Mg are preferable. Lauric acid, myristic acid and palmitic acid are more preferable. Palmitic acid is most preferable.

In the lipo-amino acid composition, each of the fatty acid (or a salt thereof) and any of the components (a) to (c) may represent 0.5% by weight or more, preferably 5% by weight or more, more preferably 10% by weight or more, relative to the total weight of the lipo-amino acid composition.

It is most preferable that the lipo-amino acid composition comprises all of the components (a) to (c) as well as at least one fatty acid, such as a C$_{12}$-C$_{18}$ fatty acid, and/or a salt of the fatty acid.

For example, a mixture of palmitic acid, palmitoyl proline, palmitoyl sarcosinate, and palmitoyl glutamate can be used as the lipo-amino acid composition. A mixture of palmitic acid, palmitoyl proline, sodium palmitoyl sarcosinate, and magnesium palmitoyl glutamate is more preferable.

In the lipo-amino acid composition comprising all of the components (a) to (c), each of the fatty acid (or a salt thereof) and any of the components (a) to (c) may represent 0.5% by weight or more, preferably 5% by weight or more, more preferably 10% by weight or more, relative to the total weight of the lipo-amino acid composition. It is possible that the lipo-amino acid composition comprises 5-50% by weight of the component (a), 5-50% by weight of the component (b), 5-25% by weight of the component (c) and 5-50% by weight of the fatty acid (or a salt thereof), relative to the total weight of the lipo-amino acid composition.

The lipo-amino acid composition can be prepared by a known method. For example, it is possible to prepare the lipo-amino acid composition in accordance with the methods described in WO 98/09611, WO 99/04757, JP-A-2000-191426 and the like. The above lipo-amino acid composition is also marketed in the name of Sepifeel One sold by Seppic in France.

The surface-treated non-spherical filler can be prepared by coating the filler with any of the components (a) to (c), a mixture of two or more of the components (a) to (c), or the lipo-amino acid composition described above.

The coating can be performed by a known method. For example, the non-spherical filler can be added into a solution of any of the components (a) to (c), a mixture of two or more of the components (a) to (c), or the lipo-amino acid composition described above; the filler is dispersed in the solution; and the dispersion is filtered, washed and dried. The solvent of the solution may be selected from water, aqueous solvents such as methanol and ethanol, and non-aqueous solvents such as ethyl acetate, depending on the nature of the components (a) to (c) and the like.

The amount of the coating depends on the type of the filler, and can be 0.1 to 30% by weight, preferably 1.0 to 10% by weight, relative to the total weight of the filler.

The filler may preferably be pre-coated with at least one oxide or hydroxide of a metal element such as aluminum, calcium, magnesium, cerium, silicon, zirconium, titanium, zinc, iron, cobalt, manganese, nickel, and tin. Aluminum hydroxide is more preferable. Further, the filler may preferably be pre-coated with a silicone compound, a fatty acid, a metal soap, a fluorine-based compound, a silane-coupling agent, and the like.

In one embodiment, the non-spherical filler coated with the lipo-amino acid composition comprising at least one fatty acid, such as a $C_{12}$-$C_{18}$ fatty acid, and/or a salt of the fatty acid, and the components (a) to (c) is/are available from the market.

For example, mica coated with palmitoyl proline, sodium palmitoyl sarcosinate, magnesium palmitoyl glutamate or palmitic acid has been marketed by Miyoshi Kasei Inc. in Japan.

In another embodiment, non-spherical fillers which have been surface-treated as follows are available from the market:
 a PEG-silicone treatment, for instance the AQ surface treatment sold by LCW;
 a lauroyllysine treatment, for instance the LL surface treatment sold by LCW;
 a lauroyllysine dimethicone treatment, for instance the LL/SI surface treatment sold by LCW;
 a disodium stearoyl glutamate treatment, for instance the NAI surface treatment sold by Miyoshi;
 a dimethicone/disodium stearoyl glutamate treatment, for instance the SA/NAI surface treatment sold by Miyoshi;
 a microcrystalline cellulose and carboxymethylcellulose treatment, for instance the AC surface treatment sold by Daito;
 an acrylate copolymer treatment, for instance the APD surface treatment sold by Daito;
 a sodium dilauramidoglutamide lysine treatment, for instance the ASL treatment sold by Daito; and
 a sodium dilauramidoglutamide lysine/isopropyl titanium triisostearate treatment, for instance the ASL treatment sold by Daito.

The non-spherical filler may be present in the composition in total amounts ranging from 1% to 50% by weight, for example, from 10% to 40% by weight, or from 20% to 30% by weight relative to the total weight of the composition.

(Additional Components)

The composition disclosed herein may comprise at least one pulverulent dyestuff, which may be chosen from pigments and nacres.

As used herein, the term "pigments" should be understood as meaning white or colored, mineral or organic particles of any shape, which are insoluble in the physiological medium, and which are intended to color the composition.

As used herein, the term "nacres" should be understood as meaning iridescent particles of any shape, for example, produced in the shell of certain molluscs or alternatively synthesized.

The pigments may be white or colored, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, such as aluminum powder or copper powder.

Among the organic pigments that may be mentioned are carbon black, pigments of D & C type, and lakes based on cochineal carmine or on barium, strontium, calcium or aluminum.

The nacreous pigments may be chosen from white nacreous pigments such as mica coated with titanium or with bismuth oxychloride, colored nacreous pigments, such as titanium mica coated with iron oxides, titanium mica coated, for example, with ferric blue or with chromium oxide, titanium mica coated with an organic pigment of the above-mentioned type, and also nacreous pigments based on bismuth oxychloride.

The composition disclosed herein may, for example, comprise at least one fatty phase, which may comprise at least one oil. This type of fatty phase is also commonly referred to as a binder, and serves, for example, as a dispersing medium for the pulverulent phase.

The oil may be chosen from the oils conventionally used as a binder in compacted powders. For example, the oil may be chosen from:
mink oil, turtle oil, soybean oil, grapeseed oil, sesame seed oil, corn oil, rapeseed oil, sunflower oil, cottonseed oil, avocado oil, olive oil, castor oil, jojoba oil, and groundnut oil;
hydrocarbon oils, such as liquid paraffin, squalane, and petroleum jelly;
fatty esters, such as isopropyl myristate, isopropyl palmitate, butyl stearate, isodecylstearate, isocetylstearate, hexyllaurate, isononyl isononanoate, 2-ethylhexyl palmitate, 2-hexyldecyl laurate, 2-octyldecyl palmitate, 2-octyldodecyl myristate, and lactate, 2-diethylhexyl succinate, diisostearyl malate, glyceryl triisostearate, and diglyceryl triisostearate;

silicone oils, such as polymethylsiloxanes, polymethylphenylsiloxan-es, polysiloxanes modified with fatty acids, with fatty alcohols or with polyoxyalkylenes, fluoro silicones, and perfluoro oils;

higher fatty acids, such as myristic acid, palmitic acid, stearic acid, behenic acid, oleic acid, linoleic acid, linolenic acid, and isostearic acid;

higher fatty alcohols, such as cetanol, stearyl alcohol, and oleyl alcohol; and poly methylfluoroalkyl dimethylsiloxanes of formula (I):

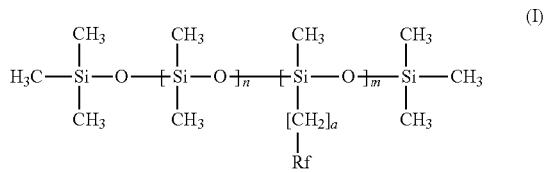

wherein:

n is an integer ranging from 5 to 90, for example, from 30 to 80 and, further, for example, from 50 to 80;

m is an integer ranging from 1 to 150, for example, from 1 to 80 and, further, for example, from 1 to 40;

a is an integer ranging from 0 to 5, and

Rf is chosen from perfluoroalkyl radicals comprising from 1 to 8 carbon atoms.

Examples of compounds of formula (I) include those sold under the names X22-819, X22-820, X22-821 and X22-822 by the company Shin-Etsu.

The composition disclosed herein may comprise the oil in an amount ranging from 1% to 20% by weight and, further, for example, from 2% to 15% by weight, relative to the total weight of the composition.

The composition may comprise at least one other common cosmetic ingredient, which may be chosen, for example, from antioxidants, fragrances, preserving agents, neutralizers, surfactants, waxes, sunscreens, vitamins, moisturizers, self-tanning compounds, and antiwrinkle active agents.

Needless to say, a person skilled in the art will take care to select this or these optional additional compound(s), and/or the amount thereof, such that the advantageous properties of the composition disclosed herein are not, or are not substantially, adversely affected by the envisaged addition(s).

These additional or optional component(s) may be present in the powdery cosmetic composition in an amount ranging from 0.1% to 15% by weight, preferably 1% to 10% by weight, more preferably 3% to 5% by weight relative to the total weight of the powdery cosmetic composition.

In one embodiment, the composition disclosed herein is an anhydrous composition. As used herein, the term "anhydrous composition" means a composition comprising no more than 2% by weight of water, for example, no more than 0.5% of water, and, for example, free of water, wherein the water is not added during the preparation of the composition, but corresponds to the residual water provided by the mixed ingredients.

The composition disclosed herein may be in the form of a compacted powder such as a powder foundation, a pressed powder and a deodorant powder. As used herein, the term "compacted powder" means a powder pressed using a manual or mechanical press.

A person skilled in the art has no difficulty in preparing the compacted powder by using well-known methods, such as a so-called dry process and wet process.

In the dry process, the components of the powdery cosmetic composition are filled into a container such as a pan. After filling, they are pressed by mechanical force provided by an electric motor, a hydraulic ram or a pneumatic cylinder, etc., in order to compact the components to prepare the compacted powder. Supersonic waves may be added, if necessary, to the components as described in JP-A-H05-70325.

In the wet process, on the other hand, the components of the powdery cosmetic composition are dispersed once in a large amount of a solvent to make a slurry. Then, the slurry is filled into a container. After the filling, the slurry is pressed by mechanical force while the solvent is removed simultaneously and/or sequentially in order to solidify the slurry.

On the other hand, the composition disclosed herein may be in the form of a loose powder.

A person skilled in the art would have no difficulty in preparing the loose powder by simply mixing the components thereof under dry conditions.

The cosmetic composition according to the present invention may be used in a cosmetic process including a step of coating a face with the composition. It is preferable to perform a process for making-up skin with the cosmetic composition according to the present invention.

EXAMPLES

The present invention will be described in more detail by way of examples, which however should not be construed as limiting the scope of the present invention.

Preparation of Composite Powder

To a solution obtained by dissolving 17.75 g of magnesium chloride in 800 ml of purified water, 20 g of talc (JA46A by ASADA SEIFUN K.K.), and 80 g of titanium oxide (A-100 by ISHIHARA SANGYO K.K.) under agitation are added and dispersed homogeneously. To this liquid dispersion, 300 ml of an aqueous solution of 8.81 g sodium hydroxide is added dropwise. After the end of dropwise addition, the reaction system is agitated and cured for one hour, filtered and washed with water to yield a powdery product, which is then crushed with a crusher. To the resulting crushed product, a solution obtained by dissolving in 50 ml of isopropanol 0.5 g of dimethicone/methicone copolymer represented by the formula of $(CH_3)_3SiO((CH_3)_2SiO)_7(CH_3HSiO)_{14}Si(CH_3)_3$ is added dropwise.

The resulting solution is agitated for one hour. The powders, thus treated, are then treated for five hours in a hot air drier maintained at 140° C., in order to obtain a composite powder.

Evaluation of Fatty Acid Solidification

The fatty acid solidification ability of the composite powder prepared as above was compared with that of magnesium carbonate powder, magnesium gluconate powder or a conventional zinc oxide composite powder (TZ Powder Type 2 marketed by Miyoshi Kasei Inc. in Japan) which has the same composition as the above composite powder except that magnesium oxide is replaced with zinc oxide.

1 g of each powder was mixed with 2 g of oleic acid, and was stirred at ambient temperature. The mixture was checked visually to determine whether the oleic acid was solidified. The results are shown in Table 1.

TABLE 1

|  | Fatty Acid Solidification |
| --- | --- |
| Composite Powder (Present Invention) | Solidified in 1-3 days |
| Magnesium Carbonate Powder | No Solidification |
| Magnesium Gluconate Powder | No Solidification |
| Composite Powder (Conventional) | Solidified in 37 minutes |

It was found that the composite powder used in the present invention can solidify fatty acid, but it took more time as compared to the conventional zinc oxide composite powder.

Example 1 and Control

The powdery cosmetic compositions according to Example 1 and the Control which have the following formulas shown in Table 2 were prepared. The amounts in Table 2 were based on percentage by weight relative to the total weight of the composition.

TABLE 2

|  | Ex. 1 | Control |
| --- | --- | --- |
| Titanium dioxide (and) lauroyl lysine | 7.00 | 7.00 |
| Titanium dioxide (and) zinc oxide (and) talc (and) dimethicone/methicone copolymer | — | 9.50 |
| Iron oxides (and) disodium stearoyl glutamate (and) aluminum hydroxide (Red) | 0.55 | 0.55 |
| Iron oxides (and) disodium stearoyl glutamate (and) aluminum hydroxide (Black) | 0.24 | 0.24 |
| Iron oxides (and) disodium stearoyl glutamate (and) aluminum hydroxide (Yellow) | 1.77 | 1.77 |
| Titanium dioxide (and) magnesium oxide (and) talc (and) dimethicone/methicone copolymer | 9.50 | — |
| Talc (and) methicone | 31.54 | 31.54 |
| Mica (and) palmitoyl proline (and) sodium palmitoyl sarcosinate (and) magnesium palmitoyl glutamate (and) aluminum hydroxide (and) palmitic acid | 22.00 | 22.00 |
| Mica (and) titanium dioxide | 2.00 | 2.00 |
| Bismuthoxychloride | 4.00 | 4.00 |
| Mica (and) dimethicone | 6.00 | 6.00 |
| Nylon-12 | 4.00 | 4.00 |
| Dimethicone/vinyl dimethicone crosspolymer | 3.20 | 3.20 |
| Caprylic/capric triglyceride | 0.92 | 0.92 |
| Bis-behenyl/isostearyl/phytosteryl dimer dilinoleyl dimer dilinoleate | 0.18 | 0.18 |
| Dimethicone | 2.30 | 2.30 |
| Ethylhexyl glycerin | 0.20 | 0.20 |
| Caprylyl glycol | 0.20 | 0.20 |
| Ethylhexyl methoxycinnamate | 3.30 | 3.30 |
| Sorbitan sesquioleate | 1.00 | 1.00 |
| Tocopheryl acetate | 0.10 | 0.10 |

In both Example 1 and the Control, the powder components shown in Table 2 were mixed in a Henschel mixer for about 10 minutes. The non-powder components (oil, UV filter and the like) shown in Table 2 were added to the mixture and mixed together for about 15 minutes. The mixture was pulverized by a Hammer mill. The pulverized powder was filtered with a mesh to form the powdery cosmetic compositions according to Example 1 and Control.

[Sensory Evaluation]

Each formulation of Example 1 and the Control in an amount of 1 g was applied to the skin of 6 panelists, and the cosmetic effects of each formulation were evaluated and compared.

Specifically, the formulation of Example 1 was applied to half of the face, and the formulation of the Control was applied to the other half of the face. The cosmetic effects of the former were compared to those of the latter. The evaluations by 6 panelists were averaged.

It was found that Example 1 and Comparative Example 1 are not significantly different and in the same level in terms of cosmetic effects related to texture.

Accordingly, it was determined that the composite powder used in Example 1 can provide substantially the same level of cosmetic effects as the conventional zinc oxide composite powder.

[Matte and Color Lasting Test]

Each of the powdery cosmetic compositions according to Example 1 and the Control was applied onto half of a face in an amount of 0.13 mg/cm$^2$, i.e., 20 mg per half of the face.

The gloss on the face was also measured by a SAMBA face system (marketed by Bossa Nova Technologies (USA)) immediately after (T(imm)) and 3 hours after (T(3 h)) the application of the powdery cosmetic composition thereto. The gloss here means the reflected light on the skin of the face. The difference in the gloss intensity (Matte) between T(imm) and T(3 h) was determined.

The color of the half face was measured with a Chromasphere (polarimetric camera) immediately after (T(imm)) and 3 hours after (T(3 h)) the application of the powdery cosmetic composition thereto. The difference (E) in color between T(imm) and T(3 h) was determined.

This test was repeated for 18 panelists, and the average was determined. The results of the tests are shown in Table 3.

TABLE 3

|  | Matte (T(3h) - T(imm)) | ΔE (T(3h) - T(imm)) |
| --- | --- | --- |
| Example 1 | 9.14 ± 3.58 | 0.80 ± 0.78 |
| Control | 9.63 ± 4.26 | 0.73 ± 0.50 |

It was found based on the above matte test that the powdery cosmetic composition according to Example 1 can provide better immediate matte effects than the powdery cosmetic composition according to the Control.

It was also found based on the above color lasting test that the powdery cosmetic composition according to Example 1 has color lasting effects which are comparable to those of the powdery cosmetic composition according to the Control.

[UV Protection Test]

The procedure of this test is outlined in the Federal Register, Vol. 64, No. 18, May 21, 1999.

Each of the powdery cosmetic compositions according to Example 1 and the Control was applied onto a 5 cm square area on the skin of a panelist in an amount of 2.0 mg/cm$^2$. Next, UV rays were irradiated to the above area from Xenon Arc Solar Simulator (Solar Light Co., USA) at 150 W. The reaction of the irradiated area was recorded for each of the powdery cosmetic compositions according to Example 1 and the Control. The SPF values for the powdery cosmetic compositions according to Example 1 and the Control were determined.

This test was repeated for 5 panelists, and the average was determined. The results of the tests are shown in Table 4.

TABLE 4

|  | SPF |
| --- | --- |
| Example 1 | 31 |
| Control | 29 |

It was found based on the UV protection test that the powdery cosmetic composition according to Example 1 can provide better UV shielding effects than the powdery cosmetic composition according to the Control.

CONCLUSION

The above evaluation and tests show that the composite powder used in the present invention can function as a preferable replacement for a conventional zinc oxide composite powder. It should be in particular remarkable that the composite powder used in the present invention solidifies fatty acid relatively slowly, but the cosmetic composition according to the present invention comprising the composite powder can exert immediate matte effects. Furthermore, the composite powder used in the present invention can enhance the UV protection property of the cosmetic composition according to the present invention.

The invention claimed is:

1. A cosmetic composition comprising a pulverulent phase comprising at least one composite powder comprising both titanium dioxide and magnesium oxide,
   wherein the pulverulent phase further comprises at least one additional filler which has been surface-treated with a surface treatment agent comprising at least one amino acid and/or a derivative thereof.

2. The cosmetic composition according to claim 1, wherein the weight ratio of the titanium dioxide to the magnesium oxide in the composite powder is greater than or equal to 1.

3. The cosmetic composition according to claim 1, wherein the composite powder further comprises at least one silicone compound.

4. The cosmetic composition according to claim 3, wherein the at least one silicone compound is chosen from methicone and dimethicone/methicone copolymer.

5. The cosmetic composition according to claim 1, wherein the composite powder further comprises at least one non-surface treated filler.

6. The cosmetic composition according to claim 5, wherein the at least one non-surface treated filler is talc.

7. The cosmetic composition according to claim 1, wherein the amount of the composite powder ranges from about 1 wt % to about 50 wt % relative to the total weight of the pulverulent phase.

8. The cosmetic composition according to claim 7, wherein the amount of the composite powder ranges from about 5 wt % to about 20 wt % relative to the total weight of the pulverulent phase.

9. The cosmetic composition according to claim 1, wherein the at least one amino acid is chosen from proline, hydroxyproline, alanine, glycine, sarcosine, aspartic acid, and glutamic acid.

10. The cosmetic composition according to claim 1, wherein the one additional filler comprises a surface-treated material comprising a material selected from talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, hydroxyapatite.

11. The cosmetic composition according to claim 10, wherein the material is mica.

12. The cosmetic composition according to claim 1, wherein the surface treatment agent comprises:
   (i) at least one first compound chosen from fatty acids and salts thereof, and
   (ii) at least one second compound chosen from:
      (a) proline, hydroxyproline and derivatives thereof;
      (b) alanine, glycine, sarcosine and derivatives thereof; and/or
      (c) aspartic acid, glutamic acid and derivatives thereof.

13. The cosmetic composition according to claim 12, wherein the fatty acids are chosen from $C_{12}$-$C_{18}$ fatty acids.

14. The cosmetic composition according to claim 12, wherein the at least one additional filler is a mica coated with a mixture of palmitic acid, palmitoyl proline, sodium palmitoyl sarcosinate, and magnesium palmitoyl glutamate.

15. The cosmetic composition according to claim 1, wherein the amount of the pulverulent phase ranges from about 10 wt % to about 99 wt % relative to the total weight of the composition.

16. The cosmetic composition according to claim 15, wherein the amount of the pulverulent phase ranges from about 50 wt % to about 90 wt % relative to the total weight of the composition.

17. The cosmetic composition according to claim 1, wherein the cosmetic composition further comprises at least one dyestuff.

18. The cosmetic composition according to claim 1, wherein the cosmetic composition further comprises at least one oil.

19. A process for making-up skin, the process comprising:
   applying to the skin a cosmetic composition comprising a pulverulent phase comprising at least one composite powder comprising both titanium dioxide and magnesium oxide,
   wherein the pulverulent phase further comprises at least one additional filler which has been surface-treated with a surface treatment agent comprising at least one amino acid and/or a derivative thereof.

* * * * *